United States Patent [19]
Imada et al.

[11] 4,362,740
[45] Dec. 7, 1982

[54] SPIRO COMPOUNDS, THEIR PRODUCTION AND USE

[75] Inventors: Isuke Imada; Hirosada Sugihara, both of Osaka; Mitsuru Kawada, Amagasaki, all of Japan

[73] Assignee: Takeda Chemical Industries, Ltd., Osaka, Japan

[21] Appl. No.: 188,834

[22] Filed: Sep. 19, 1980

[30] Foreign Application Priority Data

Sep. 25, 1979 [JP] Japan .................... 54/123433

[51] Int. Cl.³ .................... A61K 31/38; C07D 333/64
[52] U.S. Cl. .................... 424/275; 544/146; 544/376; 546/15; 548/407; 549/45; 549/52; 549/55; 549/56
[58] Field of Search .................... 549/45, 52; 546/15; 544/376, 146; 260/326.55 A; 424/275

[56] References Cited

U.S. PATENT DOCUMENTS 3,010,971 11/1961 Kaiser et al. .................... 544/376
4,105,670 8/1978 Noguchi et al. .................... 546/15
4,304,784 12/1981 Fujimara et al. .................... 424/275

FOREIGN PATENT DOCUMENTS 3084 12/1978 European Pat. Off. .

OTHER PUBLICATIONS

Okitsu, et al., "A Novel Ring Contraction of 4--Bromo-2,3-Dihydrobenzo-[b]thiepin-5(4H)-One", *Heterocycles*, vol. 6, No. 11 (1977) pp. 1877–1880.

*Primary Examiner*—Ethel G. Love
*Attorney, Agent, or Firm*—Wegner & Bretschneider

[57] ABSTRACT

New spiro compounds of the formula:

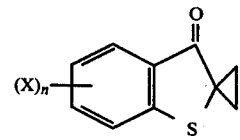

wherein n is an integer of 1 to 4, and X is halogen, lower alkyl, nitro, amino which may be substituted, hydroxyl which may be substituted, acyl, carboxyl, lower alkoxycarbonyl, carbamoyl which may be substituted, sulfamoyl which may be substituted, lower alkylthio or lower alkylsulfonyl, or two of X at the 5- and 6-positions together form —CH=CH—CH=CH—, exhibit inhibitory activity to thrombocyte aggregation and are useful for the prophylaxis or treatment of cardiovascular disturbance such as thrombosis.

12 Claims, No Drawings

SPIRO COMPOUNDS, THEIR PRODUCTION AND USE

The present invention relates to novel spiro compounds which are useful as drugs or intermediates for the drugs, to a method for producing the same, and to prophylactic and therapeutic agents for cardiovascular disturbance.

More particularly, the compounds of the present invention are novel spiro compounds of the formula:

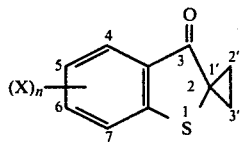

wherein
n is an integer of 1 to 4, and
X is halogen, lower alkyl, nitro, amino which may be substituted, hydroxyl which may be substituted, acyl, carboxyl, lower alkoxycarbonyl, carbamoyl which may be substituted, sulfamoyl which may be substituted, lower alkylthio or lower alkylsulfonyl,
or two of X at the 5- and 6-positions together form —CH=CH—CH=CH—,
and pharmaceutically acceptable salts thereof.

With reference to the above formula (I), examples of the halogen atom represented by X include chlorine, bromine, fluorine and iodine, and as examples of the lower alkyl group there may be mentioned $C_{1-6}$alkyl (e.g., methyl, ethyl, n-propyl, isopropyl, n-butyl, isobutyl, sec-butyl, tert-butyl, n-pentyl, isopentyl, n-hexyl, 2-methylpentyl and 2-ethylbutyl).

As examples of the amino group which may be substituted, there may be mentioned amino, hydroxyamino, mono- or di-alkylamino, acylamino, sulfonylamino and cyclic amino groups; such mono- or di-alkylamino group may include amino groups mono- or di-substituted by $C_{1-4}$alkyl, such as methylamino, ethylamino, n-propylamino, isopropylamino, n-butylamino, dimethylamino, diethylamino, di-n-propylamino, methylethylamino and the like; the acylamino group is typified by $C_{2-4}$alkanoylamino (e.g. acetylamino, propionylamino, n-butyrylamino and isobutyrylamino); the sulfonylamino group may be exemplified by $C_{1-4}$alkylsulfonylamino (e.g. methylsulfonylamino and ethylsulfonylamino); and the cyclic amino group may be for example 5- or 6-membered cyclic amino groups which may contain N or O, such as pyrrolidinyl, piperidino, piperazinyl and morpholino, wherein the piperazinyl may be further substituted on the N atom at the 4-position by $C_{1-4}$alkyl (e.g. methyl and ethyl), phenyl-$C_{1-4}$alkyl (e.g. benzyl), $C_{2-4}$alkalnoyl (e.g. acetyl and propionyl), etc.

Examples of the hydroxyl group which may be substituted include hydroxyl, alkoxy, aryloxy, aralkyloxy and acyloxy groups; such alkoxy group may preferably be alkoxy groups of 1 to 6 carbon atoms (e.g. methoxy, ethoxy, n-propoxy, isopropoxy, n-butoxy, isobutoxy, sec-butoxy and tert-butoxy groups); the aryloxy group may be exemplified by phenoxy and the like; the aralkyloxy group may be exemplified by phenyl-$C_{1-4}$alkyloxy (e.g. benzyloxy and phenethyloxy); and the acyloxy group which is preferred includes $C_{2-6}$alkanoyloxy (e.g. acetyloxy, propionyloxy, n-butyloxy and isobutyloxy groups), benzoyloxy and the like. The above alkoxy group may be substituted by carboxyl, $C_{2-6}$alkoxycarbonyl (e.g. methoxycarbonyl and ethoxycarbonyl) or carbamoyl, said carbamoyl being unsubstituted or substituted by $C_{1-4}$alkyl (e.g. methyl and ethyl) and/or $C_{5-6}$cycloalkyl (e.g. cyclopentyl and cyclohexyl).

As examples of the acyl group there may be mentioned $C_{2-6}$alkanoyl (e.g. acetyl, propionyl, n-butyryl and iso-butyryl), benzoyl and the like. Examples of the lower alkoxycarbonyl group include $C_{2-6}$alkoxycarbonyl (e.g. methoxycarbonyl, ethoxycarbonyl, n-propoxycarbonyl, iso-propoxycarbonyl and butoxycarbonyl). Examples of the carbamoyl group which may be substituted include carbamoyl and $C_{1-4}$ alkyl-substituted carbamoyl (e.g. methylcarbamoyl, ethylcarbamoyl, n-propylcarbamoyl and isopropylcarbamoyl). As examples of the sulfamoyl group which may be substituted there may be mentioned sulfamoyl, $C_{1-4}$alkyl-substituted sulfamoyl (e.g. methylsulfamoyl, ethylsulfamoyl, n-propylsulfamoyl and isopropylsulfamoyl), piperidinosulfonyl, morpholinosulfonyl and the like. The lower alkyl moiety in the lower alkylthio and lower alkylsulfonyl groups includes for example $C_{1-4}$alkyl groups (e.g. methyl, ethyl, n-propyl and isopropyl groups).

In the above formula (I), n designates an integer of 1 to 4. This is to say, the substituent, X, may exist in number of not less than 1 but not more than 4 at any substitutable positions of the benzene ring. In the case of the presence of two or more substituent groups of X, they may be the same or different.

In the present invention, a preferred embodiment provides spiro compounds of the formula (I) wherein
n is an integer of 1 to 4, and
X is halogen, $C_{1-6}$alkyl, nitro, amino, hydroxyamino, mono- or di-$C_{1-4}$alkylamino, $C_{2-4}$alkanoylamino, $C_{1-4}$alkylsulfonylamino, pyrrolidinyl, piperidino, piperazinyl, morpholino, hydroxyl, $C_{1-6}$alkoxy, phenoxy, phenyl-$C_{1-4}$alkyloxy, $C_{2-6}$alkanoyloxy, benzoyloxy, $C_{2-6}$alkanoyl, benzoyl, carboxyl, $C_{2-6}$alkoxycarbonyl, carbamoyl, $C_{1-4}$alkylcarbamoyl, sulfamoyl, $C_{1-4}$alkylsulfamoyl, piperidinosulfonyl, morpholinosulfonyl, $C_{1-4}$alkylthio or $C_{1-4}$alkylsulfonyl,
said piperazinyl being unsubstituted or substituted on the N atom at the 4-position by $C_{1-4}$alkyl, phenyl-$C_{1-4}$alkyl or $C_{2-6}$alkanoyl, and said $C_{1-6}$alkoxy being unsubstituted or substituted by carboxyl, $C_{2-6}$alkoxycarbonyl or carbamoyl which is unsubstituted or substituted by $C_{1-4}$alkyl and/or $C_{5-6}$cycloalkyl, or
two of X at the 5- and 6-positions together form —CH=CH—CH=CH—.

Among the substituent groups mentioned above for X, the halogen, $C_{1-6}$alkyl group, nitro group, amino group, $C_{2-4}$alkanoylamino group, and $C_{1-6}$alkoxy group are conveniently employed, and n is desirably 1 or 2.

The spiro compound (I) of the present invention, for example, can be produced by subjecting to decarboxylation reaction a compound of the formula:

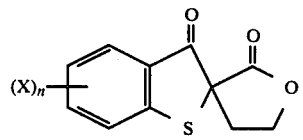

wherein n and X are as defined hereinbefore.

The reaction is normally conducted in the presence of a catalyst promoting decarboxylation, and examples of such catalyst which are conveniently employed include metal halides (e.g. sodium chloride, sodium bromide, sodium iodide, potassium bromide, potassium chloride and potassium iodide), quarternary ammonium salts (e.g. tetramethyl ammonium bromide) and the like. The reaction temperature is normally in the range of about 100° C. to 200° C. and, in particular, preferably in the range of about 140° C. to 160° C., although the reaction may be conducted at higher or lower temperatures for the purpose of controlling the rate of reaction. By replacing the reaction vessel with an inert gas (e.g. nitrogen and argon), side reactions are in some instances prevented, leading to an increase in yield. The reaction is normally conducted in an appropriate solvent, and such solvent includes any type of solvents, unless they inhibit the reaction. Normally, the solvents having higher boiling points than the reaction temperature (e.g. dimethylsulfoxide, N,N-dimethylformamide and hexamethylphosphortriamide) are conveniently employed.

Further, the substituent of the compound (I) obtained in the above reaction can also be converted into different ones by means of the reaction conventional per se. For example, the compound (I) wherein the substituent of X is amino or hydroxyamino can also be produced by subjecting the previously introduced nitro to reduction reaction. The compound (I) wherein the substituent of X is mono- or di-alkylamino is obtained through reductive alkylation of the compound (I) wherein the substituent group is amino, namely by the procedures of reducing or catalytically reducing it with the use of metal hydrides such as sodium cyanoborohydride in the presence of a carbonyl compound (e.g. formalin, acetaldehyde and acetone) or by the procedure of reacting it with alkyl halide to thereby conduct mono- or di-alkylation. Furthermore, the compound (I) having mono- or di-alkylamino can be obtained by catalytically reducing nitro-substituted compound with the use of a catalyst such as platinum oxide and Raney nickel in the presence of the above-mentioned carbonyl compound.

The objective compound (I) produced in this manner can be isolated and purified from reaction mixtures by conventional separation and purification procedures (e.g. distillation, recrystallization and column chromatography). Furthermore, the compound (I) may be isolated as a suitable salt corresponding to the type of the substituent group of X. In cases in which the substituent group is amino, mono- or di-alkyl and other groups, for example, the compounds can be isolated as acid addition salts (e.g. mineral acid salts such as hydrochloride and hydrobromide, and organic acid salts such as citrate, tartrate, maleate, fumarate and oxalate), while they can be isolated as alkali metal salts (e.g. sodium salt and potassium salt) in the case of the substituent group being carboxyl and other groups.

The spiro compounds (I) of the present invention exhibits the superior thrombocyte aggregation inhibitory activity, and are of value as the prophylactic and therapeutic agent for cardiovascular disturbance in mammals (e.g. man, rat, mouse, guinea pig, dog and pig), such as thrombosis, cerebral apoplexy (e.g. cerebral hemmorrhage, cerebral thrombosis and cerebral embolism), myocardial infarction, angina pectoris, thrombophlebitis and glomerulonephritis.

The compounds of the present invention are lowered in toxicity, and, in cases in which they are used as such drugs, the compounds (I) may be safely administered orally or parenterally, as such or as pharmaceutical compositions. The dosage depends on the subject, condition and the route of administration. The compound (I), when it is to be administered orally for example for the prophylaxis and therapy for thrombosis in an adult human, may be conveniently administered in general in a single dose of about 0.1 to 20 mg/kg body weight, about once to 3 times daily. In more particularly, it is preferred to administer it in a single dose of about 0.5 to 4 mg/kg body weight for the prophylaxis of thrombosis, and in a single dose of about 4 to 10 mg/kg body weight for the therapy for thrombosis, respectively once to 3 times daily.

The pharmaceutical composition to be used in the above-mentioned administration comprises an effective amount of the compound (I) as an active ingredient and a pharmaceutically acceptable carrier or excipient. Such composition may be presented in a form suitable for oral or parenteral administration.

Thus, the compositions for oral administration are for example the solid or liquid dosage forms, specific examples of which are tablets (including sugar coated tablets and film coating tablets), pills, granules, powders, capsules (inclusive of soft capsules), syrups, emulsions and suspensions. Such compositions are produced by the procedures conventional per se and may comprise carriers or excipients conventionally employed in the field of pharmaceutical preparations. Examples of the carriers or excipients for tablets include lactose, starch, sucrose, magnesium stearate, etc.

The compositions for parenteral administration may for example include injections, suppositories, etc. The injections include the dosage forms intended for use by intravenous and intramuscular infusions. Such injections are produced by the procedures conventional per se, or by dissolving, suspending or emulsifying the compound (I) in a sterile aqueous or oily solution normally employed for injections. The aqueous solution for injections may for example include physiological saline, isotonic solution, etc., and may be employed in combination with a suitable solubilizer such as alcohols (e.g. ethanol), polyalcohols (e.g. propyrene glycol, polyethylene glycol, etc.), non-ionic surface active agents [e.g. polysorbate 80, HCO-50 (polyoxyethylene (50 mol) adduct of hydrogenated castor oil)], etc. As examples of the oily solution there may be mentioned sesame oil and soybean oil, and they may be used in combination with a suitable solubilizer such as benzyl benzoate, benzyl alcohol, etc. The prepared injection may be normally filled into suitable ampoules. The suppositories for rectal administration are prepared by incorporating the compound (I) with a conventional excipient for suppositories.

The above-mentioned, pharmaceutical compositions for oral or parenteral administration are advantageously formulated as dosage units, each unit being adapted to supply a fixed dose of the active ingredient. Examples of such dosage unit forms are tablets, pills, capsules, injections (ampoules), suppositories, etc., and each dosage unit form normally contains 10 to 500 mg of the compound (I). Among them, an injection ampoule preferably contains 10 to 100 mg, and each of other dosage forms preferably contains 25 to 250 mg of the compound (I).

Each composition mentioned hereinbefore may contain other active ingredient or ingredients so far as they do not cause any unfavorable interaction when formulated in combination with the compound (I).

The starting compound (II) which is useful in the method according to the present invention can be produced, for example, by the process described below or a process analogous thereto.

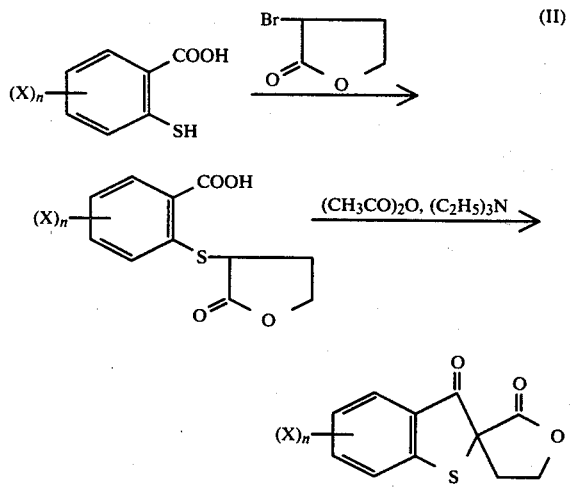

[wherein n and X are as defined hereinbefore].

Given below are Reference Examples, Examples, Test Examples and Preparation Examples to illustrate the present invention more specifically; these, however, are not intended to limit the scope of the present invention.

REFERENCE EXAMPLE 1

In 250 ml of water were dissolved 18.9 g of 5-chlorothiosalicyclic acid and 26.5 g of sodium carbonate, and 25 g of α-bromo-γ-butyrolactone was added dropwise to the solution under ice-cooling, followed by stirring at room temperature for 21 hours. 100 ml of 3 N-HCl was added to the reaction solution at room temperature to acidify the solution, and the solution was subjected to extraction with ethyl acetate. The extract was washed with aqueous saturated solution of sodium chloride and dried, and then, the solvent was distilled off. The residue was dissolved in 300 ml of toluene and heated under reflux for 2 hours while distilling off the produced water. After cooling the solution, insolubles were filtered off, and the filtrate was evaporated to dryness under reduced pressure, resulting in crude α-[(2-carboxy-4-chlorophenyl)thio]-γ-butyrolactone. The crude product was dissolved in 200 ml of acetic anhydride and 40 ml of triethylamine, and heated under a stream of nitrogen at 130° C. for 10 minutes. The reaction solution was evaporated to dryness under reduced pressure and chromatographed on a column by use of 50 g of activated carbon, 50 g of silica gel and chloroform. Recrystallization from ethanol of the resulting crude crystals yielded 7.17 g of 5-chloro-4′,5′-dihydrospiro[benzo[b]-thiophene-2(3H),3′(2′H)-furan]-3,2′-dione as pale yellow needles. Melting point: 143°–143.5° C.

Elementary analysis, for $C_{11}H_7ClO_3S$—Calcd. C, 51.87; H, 2.77. Found C, 51.87; H, 2.56.

REFERENCE EXAMPLE 2

In 200 ml of water were dissolved 14.2 g of 4-chlorothiosalicylic acid and 20 g of sodium carbonate, and 19.1 g of α-bromo-γ-butyrolactone was added dropwise to the solution under ice-cooling. After stirring the solution at room temperature for 6 hours, 35 ml of concentrated hydrochloric acid was added to the reaction solution at room temperature to acidify. After stirring at room temperature for 3 hours, the precipitate was collected, washed with water and dried, resulting in crude α-[(2-carboxy-5-chlorophenyl)thio]-γ-butyrolactone. The crude product was dissolved in 150 ml of acetic anhydride and 30 ml of triethylamine, and heated under a stream of nitrogen at 130° C. for 10 minutes. The reaction solution was evaporated to dryness under reduced pressure, and the resulting residue was chromatographed on a column of activated carbon and silica gel. Recrystallization from ethanol of the resultant crude crystals yielded 1.60 g of 6-chloro-4′,5′-dihydrospiro[-benzo[b]thiophene-2(3H),3′(2′H)-furan]-3,2′-dione as colorless needles. Melting point: 157°–158° C.

Elementary analysis, for $C_{11}H_7ClO_3S$—Calcd. C, 51.87; H, 2.77. Found C, 51.85; H, 2.68.

REFERENCE EXAMPLE 3

In 135 ml of water were dissolved 8.5 g of 5-methylthiosalicylic acid and 13.3 g of sodium carbonate, and 12.5 g of α-bromo-γ-butyrolactone was added dropwise to the solution under ice-cooling with stirring. After stirring the solution at room temperature for 15½ hours, 20 ml of concentrated hydrochloric acid was added to the solution to acidify. After stirring the solution at room temperature for 24 hours, the precipitate was collected by filtration, washed with water and dried, resulting in crude α-[(2-carboxy-4-methylphenyl)thio]-γ-butyrolactone. 5 g of the crude product was dissolved in 50 ml of acetic anhydride and 10 ml of triethylamine, and the solution was heated under a stream of nitrogen at 130° C. for 10 minutes. The reaction solution was evaporated to dryness under reduced pressure, and the residue was dissolved in ethyl acetate, washed with saturated aqueous solution of sodium chloride, and dried, followed by distilling off the solvent. The residue was chromatographed on a column of activated carbon and silica gel. Recrystallization 120°–124° C.

Elementary analysis, for $C_{12}H_{10}O_3S$—Calcd. C, 61.52; H, 4.30. Found C, 61.45; H, 4.36.

REFERENCE EXAMPLE 4

In 500 ml of water were dissolved 12.6 g of 4,5-dimethoxythiosalicylic acid and 15.6 g of sodium carbonate, and 14.6 g of α-bromo-γ-butyrolactone was added dropwise to the solution under ice-cooling with stirring. After stirring the solution at 0° C. for 30 minutes and at room temperature for 3 hours, 30 ml of concentrated hydrochloric acid was added to the solution to acidify. After stirring the solution at room temperature for 63 hours, the precipitate was recovered by filtration, washed with water and dried, resulting in 11.75 g of crude α-[(2-carboxy-4,5-dimethoxyphenyl)thio]-γ-butyrolactone. The crude product was dissolved in 200 ml of acetic anhydride and 40 ml of triethylamine, and heated under a stream of nitrogen at 130° C. for 30 minutes. The reaction solution was evaporated to dryness under reduced pressure, and the residue was chromatographed on a column of activated carbon and silica gel. Recrystallization from ethanol of the resultant crude crystals yielded 6.5 g of 5,6-dimethoxy-4′,5′-dihydrospiro[benzo[b]thiophene-2(3H),3′(2H′)-furan]-3,2′-dione as pale yellow needles. Melting point: 236°–237° C.

Elementary analysis, for $C_{13}H_{12}O_5S$—Calcd. C, 55.70; H, 4.32. Found C, 55.90; H, 4.27.

REFERENCE EXAMPLE 5

In 200 ml of water was dissolved 4.45 g of dipotassium salt of 5-nitrothiosalicylic acid, and 3.55 g of α-bromo-γ-butyrolactone was added dropwise to the solution under ice-cooling with stirring. After stirring the solution at room temperature for 3.5 hours, 10 ml of concentrated hydrochloric acid was added to the solution to acidify, and the solution was subjected to extraction with ethyl acetate. The extract was washed with water, dried and evaporated to dryness under reduced pressure, resulting in α-[(2-carboxy-4-nitrophenyl)thio]-γ-butyrolactone. The crude product was dissolved in 50 ml of acetic anhydride and 10 ml of triethylamine, and heated under a stream of nitrogen at 130° C. for 30 minutes. The reaction solution was evaporated to dryness under reduced pressure, and the residue was chromatographed on a column of activated carbon and silica gel. Recrystallization from ethanol of the resultant crude crystals yielded pale yellow needles of 5-nitro-4′,5′-dihydrospiro[benzo[b]thiophene-2(3H),3′(2′H)-furan]-3,2′-dione. Melting point: 190.5°–193.5° C.

Elementary analysis, for $C_{11}H_7NO_5S$—Calcd. C, 49.81; H, 2.66; N, 5.28. Found C, 49.82; H, 2.83; N, 5.02.

REFERENCE EXAMPLE 6

In 200 ml of water was dissolved 4.4 g of dipotassium salt of 4-nitrothiosalicylic acid, and 3.55 g of α-bromo-γ-butyrolactone was added dropwise to the solution under ice-cooling with stirring. After stirring the solution at room temperature for 14 hours, 7 ml of concentrated hydrochloric acid was added to the reaction solution at room temperature so as to acidify. The precipitate was recovered by filtration, washed with water and dried, resulting in crude α-[(2-carboxy-5-nitrophenyl)thio]-γ-butyrolactone. Recrystallization from ethanol gave pale yellow needles. Melting point: 209.5°–211.5° C.

Elementary analysis, for $C_{11}H_9NO_6S$—Calcd. C, 46.64; H, 3.20; N, 4.95. Found C, 46.55; H, 3.02; N, 5.05.

REFERENCE EXAMPLE 7

In 50 ml of acetic anhydride and 10 ml of triethylamine was dissolved 2.5 g of α-[(2-carboxy-5-nitrophenyl)thio]-γ-butyrolactone as obtained in Reference Example 6, and the solution was heated under a stream of nitrogen at 130° C. for 30 minutes. The reaction solution was evaporated to dryness under reduced pressure, and the residue was chromatographed on a column of activated carbon and silica gel. Recrystallization from ethanol of the resultant crude crystals yielded pale yellow needles of 6-nitro-4′,5′-dihydrospiro[benzo[b]thiophene-2(3H),3′(2′H)-furan]-3,2′-dione. Melting point: 184°–187° C.

Elementary analysis, for $C_{11}H_7NO_5S$—Calcd. C, 49.81; H, 2.66; N, 5.28. Found C, 49.82; H, 2.58; N, 5.28.

REFERENCE EXAMPLE 8

In 35 ml of ethyl acetate and 3.5 ml of acetic acid was dissolved 356.3 mg of 6-nitro-4′,5′-dihydrospiro[benzo[b]thiophen-2(3H),3′(2′H)-furan]-3,2′-dione as obtained in Reference Example 7, and was subjected to catalytic reduction under atmospheric pressure at room temperature in the presence of 113.3 mg of 5% palladium carbon. After absorption of hydrogen stopped, the catalyst was filtered off, and the filtrate was evaporated to dryness under reduced pressure. Recrystallization of the residue from water-acetone (7:3) yielded yellow needles of 6-hydroxyamino-4′,5′-dihydrospiro[benzo[b]thiophene-2(3H),3′(2′H)-furan]-3,2′-dione. Melting point: 184°–186° C.

Elementary analysis, for $C_{11}H_9NO_4S$—Calcd. C, 52.58; H, 3.61; N, 5.58. Found C, 52.64; H, 3.55; N, 5.68.

REFERENCE EXAMPLE 9

To a solution of 2,2′-dithio-6-methylbenzoic acid (3.05 g) in ethanol (60 ml) was added a solution of KOH(1.9 g) in ethanol (60 ml) at 70° C. with stirring. After being stirred at 100° C. for 1 hour, the mixture was evaporated in vacuo.

To a solution of the resulting residue in water (100 ml) was added α-bromo-γ-butyrolactone (3.55 g) at 0° C. with stirring. After being stirred at 0° C. for 2.5 hours and at room temperature for additional 14 hours, the mixture was filtered. The filtrate was acidified with conc. HCl (9 ml) and extracted with ethyl acetate. The extract was washed with water, dried over $Na_2SO_4$ and evaporated in vocuo to give crude α-[(2-carboxy-3-methylphenyl)thio]-γ-butyrolactone.

A mixture of this crude compound in acetic anhydride (70 ml) and triethylamine (15 ml) was heated at 130° C. for 30 minutes under a stream of $N_2$ gas with stirring. The mixture was evaporated in vacuo. The resulting residue was submitted to column chromatography on silica gel (100 g) and charcoal (20 g) eluting with $CHCl_3$ to give 4-methyl-4′,5′-dihydrospiro[benzo[b]thiophene-2(3H),3′(2′H)-furan]-3,2′-dione as colorless needles [from $C_2H_5OH$—$H_2O$ (3:2)], mp 105.5°–106.5° C. Anal. Calcd. for $C_{12}H_{10}O_3S$: C, 61.52; H, 4.30. Found: C, 61.57; H, 4.17.

REFERENCE EXAMPLE 10

6-Methyl-4′,5′-dihydrospiro[benzo[b]thiophene-2(3H),3′(2′H)-furan]-3,2′-dione was prepared by a similar procedure to that of Reference Example 9 except for the use of 2,2′-dithio-4-methylbenzoic acid. Pale yellow needles [from $C_2H_5OH$—$H_2O$ (6:5)], mp 122°–123.5° C. Anal. Calcd. for $C_{12}H_{10}O_3S$: C, 61.52; H, 4.30. Found: C, 61.57; H, 4.15.

REFERENCE EXAMPLE 11

7-Methyl-4′,5′-dihydrospiro[benzo[b]thiophene-2(3H),3′(2′H)-furan]-3,2′-dione was prepared by a similar procedure to that of Reference Example 9 except for the use of 2,2′-dithio-3-methylbenzoic acid. Pale yellow needles [from $C_2H_5OH$—$H_2O$ (1:1)], mp 98.5°–99.5° C. Anal. Calcd. for $C_{12}H_{10}O_3S$: C, 61.52; H, 4.30. Found: C, 61.61; H, 4.01.

REFERENCE EXAMPLE 12

Methyl 5-acetylsalicylate (10.0 g) was hydrogenated in the presence of 5% Pd-C (1.0 g) in ethyl acetate (200 ml) containing 70% $HClO_4$ (2 ml) at room temperature under usual pressure of $H_2$ gas with stirring. The catalyst was filtered off and the filtrate was evaporated in vacuo to give crude methyl 5-ethylsalicylate as pale brown oil.

To a solution of this crude methyl 5-ethylsalicylate (0.928 g) and 1.7 g of 1,4-diazabicyclo[2,2,2]octane (DABCO) in 10 ml of dimethylformamide (DMF) was added a solution of dimethylthiocarbamoyl chloride (2.5 g) in DMF (5 ml) at room temperature with stirring. After being stirred at room temperature for 3 days, the mixture was poured into saturated NaCl aqueous solution and extracted with ethyl acetate. The extract was washed with $H_2O$, dried over $Na_2SO_4$ and evaporated in vacuo. The resulting residue was submitted to column chromatography on silica gel (50 g) eluting with CCl$_4$-ethyl acetate (5:1) to give O-(2-carboxy-4-ethylphenyl)dimethylthiocarbamate as colorless oil. Anal. Calcd. for C$_{13}$H$_{17}$NO$_3$S: C, 58.40; H, 6.41; N, 5.24. Found: C, 58.43; H, 6.24; N, 5.41.

O-(2-Carbomethoxy-4-ethylphenyl)dimethylthiocarbamate (1.1 g) was heated at 200° C. for 16 hours. After being cooled to room temperature, the mixture was submitted to column chromatography on silica gel (50 g) eluting with CCl$_4$-ethyl acetate (2:1) to give S-(2-carbomethoxy-4-ethylphenyl)-dimethylthiocarbamate (627 mg) as colorless oil. Anal. Calcd. for C$_{13}$H$_{17}$NO$_3$S: C, 58.40; H, 6.41; N, 5.24. Found: C, 58.44; H, 6.39; N, 5.32. To a solution of the above compound (2.14 g) in ethanol (60 ml) was added a solution of KOH(4.4 g) in ethanol (100 ml) at room temperature with stirring. After being heated at 100° C. for 1 hour, the mixture was evaporated in vacuo. To a solution of the resulting residue in H$_2$O (100 ml) was added α-bromo-γ-butyrolactone (10 g) at 0° C. with stirring. After stirring at room temperature for 11 hours, α-bromo-γ-butyrolactone (2 g) was added again at room temperature with stirring. After being stirred at room temperature for 3 hours, the mixture was filtered. The filtrate was added to conc. HCl (35 ml) at room temperature with stirring. The resulting precipitate was collected, washed with H$_2$O, dried and recrystallized from benzene to give α-[(2-carboxy-4-ethylphenyl)thio]-γ-butyrolactone as colorless needles, mp 167°–169.5° C. Anal. Calcd. for C$_{13}$H$_{14}$O$_4$S: C, 58.63; H, 5.30. Found: C, 58.38; H, 5.20.

A mixture of α-[(2-carboxy-4-ethylphenyl)thio]-γ-butyrolactone (1.0 g) in acetic anhydride (30 ml) and triethylamine (6 ml) was heated at 130° C. for 30 minutes under a stream of N$_2$ gas with stirring. The mixture was evaporated in vacuo. The resulting residue was submitted to column chromatography on silica gel (20 g) and charcoal (5 g) eluting with CHCl$_3$ to give 5-ethyl-4',5'-dihydrospiro[benzo[b]thiophene-2(3H),3'(2'H)-furan]-3,2'-dione as colorless oil. Anal. Calcd. for C$_{13}$H$_{12}$O$_3$S: C, 62.88; H, 4.87. Found: C, 62.83; H, 4.83.

REFERENCE EXAMPLE 13

5-Acetyl-4',5'-dihydrospiro[benzo[b]thiophene-2(3H),3'(2'H)-furan]-3,2'-dione was prepared by a similar procedure to that of Reference Example 12. Colorless needles, mp 139°–140.5° C. Anal. Calcd. for C$_{13}$H$_{10}$O$_4$S: C, 59.53; H, 3.84. Found: C, 59.15; H, 4.14.

REFERENCE EXAMPLE 14

4-[5-[4',5'-Dihydrospiro[benzo[b]thiophene-2(3H),3'(2'H)-furan]-3,2'-dioxo]oxy]butyric acid was prepared by a similar procedure to that of Reference Example 12. Pale yellow needles, mp 124°–126° C. Anal. Calcd. for C$_{15}$H$_{14}$O$_6$S: C, 55.89; H, 4.38. Found: C, 55.98; H, 4.39.

REFERENCE EXAMPLE 15

5-Nitro-4',5'-dihydrospiro[benzo[b]thiophene-2(3H),3'(2'H)-furan]-3,2'-dione (1.0 g) was hydrogenated in the presence of 5% Pd-C (0.35 g) in acetic acid (100 ml) at room temperature under usual pressure of H$_2$ gas with stirring. The catalyst was filtered off and the filtrate was evaporated in vacuo. The resulting residue was recrystallized from benzene to give 5-amino-4',5'-dihydrospiro[benzo[b]thiophene-2(3H),3'(2'H)-furan]-3,2'-dione as yellow needles, mp 187°–190° C. Anal. Calcd. for C$_{11}$H$_9$NO$_3$S: C, 56.15; H, 3.86; N, 5.96. Found: C, 56.61; H, 3.73; N, 5.96.

REFERENCE EXAMPLE 16

To ClSO$_3$H (15 ml) was added 4',5'-dihydrospiro[benzo[b]thiophene-2(3H),3'(2'H)-furan]-3,2'-dione (5.0 g) at 0° C. with stirring. After being stirred at room temperature for 1.5 hours, the mixture was poured into ice and extracted with ethyl acetate. The extract was washed with H$_2$O, dried over Na$_2$SO$_4$ and evaporated in vacuo. To a solution of the resulting residue in 100 ml of tetrahydrofuran (THF) was added 25% NH$_4$OH (3.2 ml) at 0° C. with stirring. After being stirred at 0° C. for 30 minutes, the mixture was dried over Na$_2$SO$_4$ and evaporated in vacuo. The resulting residue was recrystallized from ethanol to give 5-sulfamoyl-4',5'-dihydrospiro[benzo[b]thiophene-2(3H),3'(2'H)-furan]-3,2'-dione as colorless needles, mp 199°–201° C. Anal. Calcd. for C$_{11}$H$_9$NO$_5$S$_2$: C, 44.14; H, 3.03; N, 4.68. Found: C, 44.09; H, 3.22; N, 4.49.

REFERENCE EXAMPLE 17

5-Piperidinosulfonyl-4',5'-dihydrospiro[benzo[b]thiophene-2(3H),3'(2'H)-furan]-3,2'-dione was prepared by a similar procedure to that of Reference Example 16 except for the use of piperidine. Colorless needles [from C$_2$H$_5$OH—H$_2$O (1:1)], mp 159°–161° C. Anal. Calcd. for C$_{16}$H$_{17}$NO$_5$S$_2$: C, 52.30; H, 4.66; N, 3.81. Found: C, 52.14; H, 4.56; N, 3.77.

REFERENCE EXAMPLE 18

5-Morpholinosulfonyl-4',5'-dihydrospiro[benzo[b]thiophene-2(3H),3'(2'H)-furan]-3,2'-dione was prepared by a similar procedure to that of Reference Example 16 except for the use of morpholine. Colorless needles [from H$_2$O-acetone (3:1)], mp 220°–222.5° C. Anal. Calcd. for C$_{15}$H$_{15}$NO$_6$S$_2$: C, 48.77; H, 4.09; N, 3.79. Found: C, 48.81; H, 4.04; N, 4.08.

EXAMPLE 1

In 13 ml of dimethylsulfoxide were dissolved 2.55 g of 5-chloro-4',5'-dihydrospiro[benzo[b]thiophene-2(3H),3'(2'H)-furan]-3,2'-dione as obtained in Reference Example 1 and 586.1 mg of sodium chloride, and heated under a stream of nitrogen at 150° C. for 30 minutes. After cooling, the reaction solution was poured into 200 ml of saturated aqueous solution of sodium chloride and subjected to extraction with ethyl acetate. The extract was washed with saturated aqueous solution of sodium chloride, dried and evaporated to dryness under reduced pressure. The residue was chromatographed on a column of silica gel (100 g) with the use of carbon tetrachloride. Recrystallization of the resultant crystals from n-hexane-benzene (5:1) yielded 1.15 g of colorless needles of 5-chlorospiro[benzo[b]thiophene-2(3H),1'-cyclopropan]-3-one. Melting point: 106°–107° C.

Elementary analysis, for C$_{10}$H$_7$ClOS— Calcd. C, 57.01; H, 3.35. Found: C, 56.91; H, 3.09.

EXAMPLE 2

In 20 ml of dimethylsulfoxide were dissolved 1.8999 g of 6-chloro-4',5'-dihydrospiro[benzo[b]thiophene-2(3H),3'(2'H)-furan]-3,2'-dione as obtained in Reference Example 2 and 491 mg of sodium chloride, and heated under a stream of nitrogen at 150° C. for 1¼ hours. After cooling, the solution was poured into 300 ml of saturated aqueous solution of sodium chloride and subjected to extraction with ethyl acetate. The extract was washed with saturated aqueous solution of sodium chloride, dried and evaporated to dryness under reduced pressure. The residue was chromatographed on a column of silica gel (100 g) with the use of carbon tetrachloride. Recrystallization of the resultant crude crystals from methanol-water (22:5) yielded 1.08 g of colorless needles of 6-chlorospiro[benzo[b]thiophene-2(3H),1'-cyclopropan]-3-one. Melting point: 84° C.

Elementary analysis, for $C_{10}H_7ClOS$— Calcd. C, 57.01; H, 3.35. Found C, 56.91; H, 3.20.

EXAMPLE 3

In 10 ml of dimethylsulfoxide were dissolved 1.0 g of 5-methyl-4',5'-dihydrospiro[benzo[b]thiophene-2(3H),3'(2'H)-furan]-3,2'-dione as obtained in Reference Example 3 and 282.6 mg of sodium chloride, and the solution was heated under a stream of nitrogen at 150° C. for 1.5 hours. After cooling, the reaction solution was poured into 200 ml of saturated aqueous solution of sodium chloride and subjected to extraction with ethyl acetate. The extract was washed with saturated aqueous solution of sodium chloride, dried and evaporated to dryness under reduced pressure. The residue was chromatographed on a column with the use of 10 g of activated carbon, 30 g of silica gel and carbon tetrachloride-methylene chloride (1:1). Recrystallization of the resultant crude crystals from ethanol-water (2:1) yielded 604.5 mg of colorless needles of 5-methylspiro[benzo[b]thiophene-2(3H),1'-cyclopropan]-3-one. Melting point: 68°–69.5° C.

Elementary analysis, for $C_{11}H_{10}OS$— Calcd. C, 69.44; H, 5.30. Found: C, 69.67; H, 5.31.

EXAMPLE 4

In 30 ml of dimethylsulfoxide were dissolved 2.8 g of 5,6-dimethoxy-4',5'-dihydrospiro[benzo[b]thiophene-2(3H),3'(2'H)-furan]-3,2'-dione as obtained in Reference Example 4 and 656.6 mg of sodium chloride, and the solution was heated under a stream of nitrogen at 150° C. for 2.5 hours. After cooling, the reaction solution was poured into 400 ml of saturated aqueous solution of sodium chloride, and the resulting precipitate was recovered by filtration, washed with water and dried. The product obtained was chromatographed on a column with the use of 3 g of activated carbon, 15 g of silica gel and chloroform. Recrystallization of the resultant crude crystals from ethanol-water (2:1) yielded 2.1 g of colorless needles of 5,6-dimethoxyspiro[benzo[b]thiophene-2(3H),1'-cyclopropan]-3-one. Melting point: 167.5°–169.5° C.

Elementary analysis, for $C_{12}H_{12}O_3S$— Calcd. C, 60.99; H, 5.12. Found: C, 61.10; H, 5.04.

EXAMPLE 5

In 10 ml of dimethylsulfoxide were dissolved 503.3 mg of 5-nitro-4',5'-dihydrospiro[benzo[b]thiophene-2(3H),3'(2'H)-furan]-3,2'-dione as obtained in Reference Example 5 and 130.1 mg of sodium chloride, and the solution was heated under a stream of nitrogen at 150° C. for 30 minutes. After cooling, the reaction solution was poured into 300 ml of saturated aqueous solution of sodium chloride and subjected to extraction with ethyl acetate. The extract was washed with saturated aqueous solution of sodium chloride, dried and evaporated to dryness under reduced pressure. The residue was chromatographed on a column of activated carbon and silica gel. Recrystallization of the resultant crude crystals yielded pale yellow needles of 5-nitrospiro[benzo[b]thiophene-2(3H),1'-cyclopropan]-3-one. Melting point: 126.5°–127.5° C.

Mass spectrum (m/e): 221 (M+)

Elementary analysis, for $C_{10}H_7NO_3S$— Calcd. C, 54.29; H, 3.19; N, 6.33. Found: C, 54.48; H, 3.39; N, 6.31.

EXAMPLE 6

In 4 ml of dimethylsulfoxide (DMSO) were dissolved 179.9 mg of 6-hydroxyamino-4',5'-dihydrospiro[benzo[b]thiophene-2(3H),3'(2'H)-furan]-3,2'-dione and 101.4 mg of sodium chloride, and the solution was heated under a stream of nitrogen at 150° C. for 2.5 hours. After cooling, the reaction solution was poured into 200 ml of saturated aqueous solution of sodium chloride and subjected to extraction with ethyl acetate. The extract was washed with saturated aqueous solution of sodium chloride, dried and evaporated to dryness under reduced pressure. The residue was chromatographed on a column of activated carbon and silica gel. Recrystallization of the resultant crude crystals from ethanol yielded pale yellow needles of 6-aminospiro[benzo[b]thiophene-2(3H),1'-cyclopropan]-3-one. Melting point: 196°–200° C.

Mass spectrum (m/e): 191 (M+)

EXAMPLE 7

In 2 ml of acetic acid and 2 ml of acetic anhydride was dissolved 9.5 mg of 6-aminospiro[benzo[b]thiophene-2(3H),1'-cyclopropan]-3-one as obtained in Example 6, and the solution was stirred at room temperature for 10 minutes. The reaction solution was evaporated to dryness under reduced pressure, and the residue was chromatographed on a column of silica gel. Recrystallization of the resultant crude crystals from ethanol-water (1:2) yielded colorless needles of 6-acetylaminospiro[benzo[b]thiophene-2(3H),1'-cyclopropan]-3-one. Melting point: 195°–196.5° C.

Mass spectrum (m/e): 233 (M+)

Elementary analysis, for $C_{12}H_{11}NO_2S \cdot H_2O$— Calcd. C, 57.35; H, 5.21; N, 5.58. Found: C, 57.34; H, 5.16; N, 5.63.

EXAMPLE 8

A mixture of 4-methyl-4',5'-dihydrospiro[benzo[b]thiophene-2(3H),3'(2'H)-furan]-3,2'-dione (505 mg) obtained in Reference Example 9 and NaCl (261 mg) in DMSO (15 ml) was heated at 150° C. for 2.5 hours under a stream of $N_2$ gas. After being cooled to room temperature, the mixture was poured into saturated NaCl aqueous solution. The resulting precipitate was collected, washed with $H_2O$ and dried. This precipitate was submitted to column chromatography on silica gel (45 g) and charcoal (1.5 g) eluting with $CCl_4$-ethyl acetate (20:1) to give 4-methylspiro[benzo[b]thiophene-2(3H),1'-cyclopropan]-3-one as colorless needles [from $C_2H_5OH$—$H_2O$ (3:1)], mp 128°–128.5° C. Anal. Calcd. for $C_{11}H_{10}OS$: C, 69.44; H, 5.30. Found: C, 69.69; H, 5.18.

EXAMPLE 9

6-Methylspiro[benzo[b]thiophene-2(3H),1'-cyclopropan]-3-one was prepared by a similar procedure to that of Example 8 except for the use of 6-methyl-4',5'-dihydrospiro[benzo[b]thiophene-2(3H),3'(2'H)-furan]-3,2'-dione obtained in Reference Example 10. Pale brown oil. Anal. Calcd. for $C_{11}H_{10}OS$: C, 69.44; H, 5.30. Found: C, 69.37; H, 5.20.

EXAMPLE 10

7-Methylspiro[benzo[b]thiophene-2(3H),1'-cyclopropan]-3-one was prepared by a similar procedure to that of Example 8 except for the use of 7-methyl-4',5'-dihydrospiro[benzo[b]thiophene-2(3H),3'(2'H)-furan]-3,2'-dione obtained in Reference Example 11. Pale yellow needles [from $C_2H_5OH$—$H_2O$ (1:1)], mp 74°–75° C. Anal. Calcd. for $C_{11}H_{10}OS$: C, 69.44; H, 5.30. Found: C, 69.32; H, 5.07.

EXAMPLE 11

5-Ethylspiro[benzo[b]thiophene-2(3H),1'-cyclopropan]-3-one was prepared by a similar procedure to that of Example 8 except for the use of 5-ethyl-4',5'-dihydrospiro[benzo[b]thiophene-2(3H),3'(2'H)-furan]-3,2'-dione obtained in Reference Example 12. Colorless oil. Anal. Calcd. for $C_{12}H_{12}OS$: C, 70.55; H, 5.92. Found: C, 70.68; H, 5.82.

EXAMPLE 12

5-Acetylspiro[benzo[b]thiophene-2(3H),1'-cyclopropan]-3-one was prepared by a similar procedure to that of Example 8 except for the use of 5-acetyl-4',5'-dihydrospiro[benzo[b]thiophene-2(3H),3'(2'H)-furan]-3,2'-dione obtained in Reference Example 13. Colorless prisms, mp 127.5°–129° C. Anal. Calcd. for $C_{12}H_{10}O_2S$: C, 66.03; H, 4.62. Found: C, 66.01; H, 4.42.

EXAMPLE 13

4-[5-[Spiro(benzo[b]thiophene-2(3H),1'-cyclopropan)-3-oxo]oxy]butyric acid was prepared by a similar procedure to that of Example 8 except for the use of 4-[5-[4',5'-dihydrospiro(benzo[b]thiophene-2(3H),3'(2'H)-furan)-3,2'-dioxo]oxy]butyric acid obtained in Reference Example 14. Pale yellow needles, mp 131°–132° C. Anal. Calcd. for $C_{14}H_{14}O_4S$: C, 60.41; H, 5.07. Found: C, 60.63; H, 5.05.

EXAMPLE 14

To a solution of 4-[5-[spiro(benzo[b]thiophene-2(3H),1'-cyclopropan)-3-oxo]oxy]butyric acid (259 mg) obtained in Example 13 in dry THF (40 ml) and triethylamine (6 ml) was added methyl chloroformate (4 ml) at −20° C. to 31 15° C. with stirring. After stirring the solution at −20° C. to −15° C. for 15 minutes, N-methylcyclohexylamine was added to the mixture at the same temperature with stirring. After being stirred at 5° C. for 11 hours, the mixture was filtered. The filtrate was evaporated in vacuo. The resulting residue was submitted to column chromatography on silica gel eluting with $CCl_4$-ethyl acetate (5:1 and 2:1) to give N-cyclohexyl-N-methyl-4-[5-[spiro(benzo[b]thiophene-2(3H),1'-cyclopropan)-3-oxo]oxy]butyramide as colorless needles, mp 102°–104° C. Anal. Calcd. for $C_{21}H_{27}NO_3S$: C, 67.52; H, 7.29; N, 3.75. Found: C, 66.81; H, 7.41; N, 3.80.

EXAMPLE 15

A mixture of 5-amino-4',5'-dihydrospiro[benzo[b]thiophene-2(3H),3'(2'H)-furan]-3,2'-dione (40.4 mg) obtained in Reference Example 15 and NaCl (20.6 mg) in DMSO (2.0 ml) was heated at 150° C. for 3 hours under a stream of $N_2$ gas with stirring. After being cooled to room temperature, the mixture was poured into saturated NaCl aqueous solution and extracted with ethyl acetate. The extract was washed with $H_2O$, dried over $Na_2SO_4$ and evaporated in vacuo. The resulting residue was recrystallized from ethanol to give 5-aminospiro[benzo[b]thiophene-2(3H),1'-cyclopropan]-3-one as pale yellow needles, mp 147.5°–149.5° C. Anal. Calcd. for $C_{10}H_9NOS$: C, 62.80; H, 4.74; N, 7.33. Found: C, 62.45; H, 4.75; N, 7.06.

EXAMPLE 16

To a solution of 5-aminospiro[benzo[b]thiophene-2(3H),1'-cyclopropan]-3-one (200 mg) obtained in Example 15 in acetic acid (8 ml) was added acetic anhydride (8 ml) at room temperature with stirring. After being stirred for 30 minutes, the mixture was evaporated in vacuo. The resulting residue was recrystallized from $C_2H_5OH$-$H_2O$ (2:1) to give 5-acetylaminospiro[benzo[b]thiophene-2(3H),1'-cyclopropan-3-one as pale yellow needles, mp 205°–208.5° C. Anal. Calcd. for $C_{12}H_{11}NO_2S$: C, 61.78; H, 4.75; N, 6.01. Found: C, 61.42, H, 4.81; N, 5.73.

EXAMPLE 17

5-Sulfamoylspiro[benzo[b]thiophene-2(3H),1'-cyclopropan]-3-one was prepared by a similar procedure to that of Example 8 except for the use of 5-sulfamoyl-4',5'-dihydrospiro[benzo[b]thiophene-2(3H),3'(2'H)-furan]-3,2'-dione obtained in Reference Example 16. Pale yellow needles (from $C_2H_5OH$), mp 256°–258° C. (decomp.) Anal. Calcd. for $C_{10}H_9NO_3S_2$: C, 47.04; H, 3.55; N, 5.49. Found: C, 47.18; H, 3.57; N, 5.44.

EXAMPLE 18

5-Piperidinosulfonylspiro[benzo[b]thiophene-2(3H),1'-cyclopropan]-3-one was prepared by a similar procedure to that of Example 8 except for the use of 5-piperidinosulfonyl 4',5'-dihydrospiro[benzo[b]thiophene-2(3H),3'(2'H)-furan]-3,2'-dione obtained in Reference Example 17. Colorless prisms (from $C_2H_5OH$), mp 155.5°–157° C. Anal. Calcd. for $C_{15}H_{17}NO_3S$: C, 55.70; H, 5.30; N, 4.33. Found: C, 55.74; H, 5.34; N, 4.50.

EXAMPLE 19

5-Morpholinosulfonylspiro[benzo[b]thiophene-2(3H),1'-cyclopropan]-3-one was prepared by a similar procedure to that of Example 8 except for the use of 5-morpholinosulfonyl-4',5'-dihydrospiro[benzo[b]thiophene-2(3H),3'(2'H)-furan]3,2'-dione obtained in Reference Example 18. Colorless needles (from acetone —$H_2O$), mp 162.5°–165° C. Anal. Calcd. for $C_{14}H_{15}NO_4S$: C, 51.67; H, 4.65; N, 4.31. Found: C, 51.45; H, 4.55; N, 4.41.

TEST EXAMPLE

The platelet aggregation inhibitory activity of the compound of the present invention.

[Testing procedure]

With the use of an injection syringe containing a 3.15% citric acid solution (in the proportion of 1 against 9 of blood) as an anticoagulant, a blood sample was taken directly from the heart of a male rabbit, and then centrifuged at room temperature and 1,000 r.p.m. for 10 minutes to obtain a platelet rich plasma (PRP).

Using 5-methylspiro[benzo[b]thiophene-2(3H),1'-cyclopropan]-3-one as a test drug, the test drug solution was prepared as follows: The test drug was dissolved in dimethylsulfoxide to a concentration of 20 mM, and the solution was diluted to a test drug concentration of $6 \times 10^{-5}$ M or $1.2 \times 10^{-4}$ M by adding Tris-HCl buffer (50 mM: pH 7.5). To 250 μl of the above PRP was added 25 μl of the test drug solution, and the aggregation of platelets, upon addition of arachidonic acid of 0.42 mM as the final concentration or of 25 μl of 217 μg/ml collagen, was measured with an aggregation meter (manufactured by Rika Denki K.K., Japan). The activity of the test drug was estimated by determining the inhibition rate for the maximum light transmittance of the control PRP which is altered by arachidonic acid or collagen.

[Test results]

Inhibition rate of the tested compound to the platelet aggregation by arachidonic acid:

| $5 \times 10^{-6}$M | 15% |
| --- | --- |

Inhibition rate of the tested compound to the platelet aggregation by collagen:

| $5 \times 10^{-6}$M | 23% |
| --- | --- |
| $1 \times 10^{-5}$M | 48% |

PREPARATION EXAMPLE

Tablet

Composition:

| (1) 5-Methylspiro[benzo[b]thiophene-2(3H),1'-cyclopropan]-3-one | 25 g |
| --- | --- |
| (2) Lactose | 70 g |
| (3) Corn starch | 20 g |
| (4) Hydroxypropylcellulose | 4 g |
| (5) Magnesium stearate | 1 g |
| 1000 tablets: | 120 g |

Preparation:

The mixture of (1), (2) and (3) was moistened with a 10% aqueous solution of (4), granulated through a 1.5 mm screen and dried at 40° C. in vacuo. The resultant granulates were passed once more through the screen, mixed with (5) and pressed to produce 1000 tablets, each tablet containing 25 mg of (1) and having 7 mm in diameter.

What we claim is:

1. A compound of the formula:

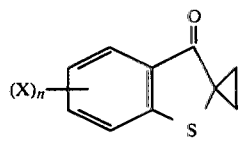

wherein
n is an integer of 1 to 4, and
X is halogen, $C_{1-6}$alkyl, nitro, amino, hydroxyamino, mono- or di-$C_{1-4}$alkylamino, $C_{2-4}$alkanoylamino, $C_{1-4}$alkylsulfonylamino, hydroxyl, $C_{1-6}$alkoxy, phenoxy, phenyl-$C_{1-4}$alkyloxy, $C_{2-6}$alkanoyloxy, benzoyloxy, $C_{2-6}$alkanoyl, benzoyl, carboxyl, $C_{2-6}$alkoxycarbonyl, carbamoyl, $C_{1-4}$alkylcarbamoyl, sulfamoyl, $C_{1-4}$alkylsulfamoyl, piperidinosulfonyl, morpholinosulfonyl, $C_{1-4}$alkylthio or $C_{1-4}$alkylsulfonyl,
said $C_{1-6}$alkoxy being unsubstituted or substituted by carboxyl, $C_{2-6}$alkoxycarbonyl or carbamoyl which is unsubstituted or substituted by $C_{1-4}$alkyl and/or $C_{5-6}$cycloalkyl, or two of X at the 5- and 6-positions together form —CH=CH—CH=CH—,
or a pharmaceutically acceptable salt thereof.

2. A compound according to claim 1, wherein n is 1 or 2.

3. A compound according to claim 1, wherein X is halogen, $C_{1-6}$alkyl, nitro, amino, $C_{2-4}$alkanoylamino, $C_{1-6}$alkoxy, $C_{2-6}$alkanoyl, sulfamoyl, piperidinosulfonyl or morpholinosulfonyl, said $C_{1-6}$alkoxy being unsubstituted or substituted by carboxyl or N-cyclohexyl-N-methylcarbamoyl.

4. A compound according to claim 3, wherein X is $C_{1-4}$alkyl, $C_{1-4}$alkoxy or $C_{2-4}$alkanoyl.

5. The compound according to claim 1, which is 5-methylspiro[benzo[b]thiophene-2(3H),1'-cyclopropan]-3-one.

6. The compound according to claim 1, which is 5,6-dimethoxyspiro[benzo[b]thiophene-2(3H),1'-cyclopropan]-3-one.

7. The compound according to claim 1, which is 5-acetylspiro[benzo[b]thiophene-2(3H),1'-cyclopropan]-3-one.

8. The compound according to claim 1, which is 5-acetylaminospiro[benzo[b]thiophene-2(3H),1'-cyclopropan]-3-one.

9. A pharmaceutical composition suitable for the prophylaxis or treatment of thrombosis, which comprises as an active ingredient an antithrombotically effective amount of a compound of the formula:

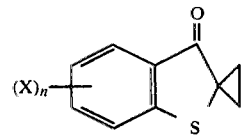

wherein
n is an integer of 1 to 4, and
X is halogen, $C_{1-6}$alkyl, nitro, amino, hydroxyamino, mono- or di-$C_{1-4}$alkylamino, $C_{2-4}$alkanoylamino, $C_{1-4}$alkylsulfonylamino, hydroxyl, $C_{1-6}$alkoxy, phenoxy, phenyl-$C_{1-4}$alkyloxy, $C_{2-6}$alkanoyloxy, benzoyloxy, $C_{2-6}$alkanoyl, benzoyl, carboxyl, $C_{2-6}$alkoxycarbonyl, carbamoyl, $C_{1-4}$alkylcarbamoyl, sulfamoyl, $C_{1-4}$alkylsulfamoyl, piperidinosulfonyl, morpholinosulfonyl, $C_{1-4}$alkylthio or $C_{1-4}$alkylsulfonyl,
said $C_{1-6}$alkoxy being unsubstituted or substituted by carboxyl, $C_{2-6}$alkoxycarbonyl or carbamoyl which is unsubstituted or substituted by $C_{1-4}$alkyl and/or $C_{5-6}$cycloalkyl, or two of X at the 5- and 6-positions together form —CH=CH—CH=CH—,
or a pharmaceutically acceptable salt thereof,
in association with a pharmaceutically acceptable carrier or excipient therefor.

10. A method for the prophylaxis or treatment of thrombosis in a mammal which comprises administering to said mammal an antithrombotically effective amount of a compound of the formula:

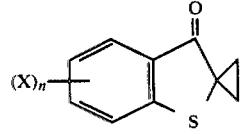

wherein n is an integer of 1 to 4, and

X is halogen, C$_{1-6}$alkyl, nitro, amino, hydroxyamino, mono- or di-C$_{1-4}$alkylamino, C$_{2-4}$alkanoylamino, C$_{1-4}$alkylsulfonylamino, hydroxyl, C$_{1-6}$alkoxy, phenoxy, phenyl-C$_{1-4}$alkyloxy, C$_{2-6}$alkanoyloxy, benzoyloxy, C$_{2-6}$alkanoyl, benzoyl, carboxyl, C$_{2-6}$alkoxycarbonyl, carbamoyl, C$_{1-4}$alkylcarbamoyl, sulfamoyl, C$_{1-4}$alkylsulfamoyl, piperidinosulfonyl, morpholinosulfonyl, C$_{1-4}$alkylthio or C$_{1-4}$alkylsulfonyl, said C$_{1-6}$alkoxy being unsubstituted or substituted by carboxyl, C$_{2-6}$alkoxycarbonyl or carbamoyl which is unsubstituted or substituted by C$_{1-4}$alkyl and/or C$_{5-6}$cycloalkyl, or two of X at the 5- and 6-positions together form —CH=CH—CH=CH—, or a pharmaceutically acceptable salt thereof.

11. A compound of the formula:

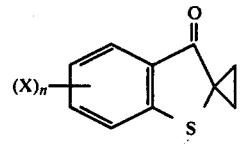

wherein n is an integer of 1 to 4, and

X is halogen, nitro, amino, hydroxyamino, mono- or di-C$_{1-4}$alkylamino, C$_{2-4}$alkanoylamino, C$_{1-4}$alkylsulfonylamino, hydroxyl, C$_{1-6}$alkoxy, phenoxy, phenyl-C$_{1-4}$alkyloxy, C$_{2-6}$alkanoyloxy, benzoyloxy, C$_{2-6}$alkanoyl, benzoyl, carboxyl, C$_{2-6}$alkoxycarbonyl, carbamoyl, C$_{1-4}$alkylcarbamoyl, sulfamoyl, C$_{1-4}$alkylsulfamoyl, piperidinosulfonyl, morpholinosulfonyl, C$_{1-4}$alkylthio or C$_{1-4}$alkylsulfonyl, said C$_{1-6}$alkoxy being unsubstituted or substituted by carboxyl, C$_{2-6}$alkoxycarbonyl or carbamoyl which is unsubstituted or substituted by C$_{1-4}$alkyl and/or C$_{5-6}$cycloalkyl, or two of X at the 5- and 6-positions together form —CH=CH—CH=CH—, or a pharmaceutically acceptable salt thereof.

12. A compound according to claim 1, wherein n is 1 and X is methyl.

* * * * *